United States Patent
Xu et al.

(10) Patent No.: US 9,301,925 B2
(45) Date of Patent: Apr. 5, 2016

(54) INKJET PRINTING OF TISSUES AND CELLS

(71) Applicant: Wake Forest University Health Sciences, Winston-Salem, NC (US)

(72) Inventors: Tao Xu, El Paso, TX (US); James J. Yoo, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/644,678

(22) Filed: Mar. 11, 2015

(65) Prior Publication Data

US 2015/0182471 A1    Jul. 2, 2015

Related U.S. Application Data

(62) Division of application No. 14/185,090, filed on Feb. 20, 2014, now Pat. No. 9,005,972, which is a division of application No. 12/370,921, filed on Feb. 13, 2009, now Pat. No. 8,691,274.

(60) Provisional application No. 61/028,761, filed on Feb. 14, 2008.

(51) Int. Cl.
| | |
|---|---|
| *C12N 5/02* | (2006.01) |
| *C12N 11/04* | (2006.01) |
| *A61K 9/50* | (2006.01) |
| *A61L 27/38* | (2006.01) |
| *A61L 27/50* | (2006.01) |
| *A61L 27/58* | (2006.01) |
| *B41J 3/407* | (2006.01) |
| *C12N 11/08* | (2006.01) |
| *D01D 5/00* | (2006.01) |
| *D01F 6/62* | (2006.01) |
| *A61K 35/32* | (2015.01) |
| *A61K 35/34* | (2015.01) |
| *A61K 35/36* | (2015.01) |
| *A61F 2/06* | (2013.01) |

(52) U.S. Cl.
CPC .............. *A61K 9/5089* (2013.01); *A61K 35/32* (2013.01); *A61K 35/34* (2013.01); *A61K 35/36* (2013.01); *A61L 27/38* (2013.01); *A61L 27/50* (2013.01); *A61L 27/58* (2013.01); *B41J 3/407* (2013.01); *C12N 11/04* (2013.01); *C12N 11/08* (2013.01); *D01D 5/0007* (2013.01); *D01F 6/625* (2013.01); *A61F 2/062* (2013.01)

(58) Field of Classification Search
CPC ........ A61F 2/062; A61K 35/32; A61K 35/34; A61K 35/36; A61L 27/38; A61L 27/50; A61L 27/58
USPC .......... 424/93.7, 484; 435/174, 178, 182, 395
See application file for complete search history.

(56) References Cited

U.S. PATENT DOCUMENTS

| | | | |
|---|---|---|---|
| 4,680,511 A | 7/1987 | Fitzgerald et al. | |
| 5,702,444 A | 12/1997 | Struthers et al. | |
| 6,537,567 B1 | 3/2003 | Niklason et al. | |
| 6,673,597 B2 | 1/2004 | Wolf et al. | |
| 6,783,964 B2 | 8/2004 | Opara | |
| 7,051,654 B2 | 5/2006 | Boland et al. | |
| 7,097,857 B2 | 8/2006 | Tracy et al. | |
| 7,172,765 B2 | 2/2007 | Chu et al. | |
| 7,186,554 B2 | 3/2007 | Ehmann et al. | |
| 7,297,305 B2 | 11/2007 | Andrady et al. | |
| 7,323,425 B2 | 1/2008 | Chu et al. | |
| 7,326,043 B2 | 2/2008 | Joo et al. | |
| 7,625,198 B2 | 12/2009 | Lipson et al. | |
| 2004/0028875 A1 | 2/2004 | Van Rijn et al. | |
| 2004/0237822 A1* | 12/2004 | Boland et al. ................. | 101/483 |
| 2004/0258729 A1 | 12/2004 | Czernuszka et al. | |
| 2005/0175978 A1 | 8/2005 | Ramasubramanian | |
| 2006/0018966 A1 | 1/2006 | Lin et al. | |
| 2006/0085063 A1 | 4/2006 | Shastri et al. | |
| 2006/0156978 A1* | 7/2006 | Lipson et al. ................. | 118/708 |
| 2007/0003603 A1 | 1/2007 | Karandikar et al. | |

FOREIGN PATENT DOCUMENTS

| | | |
|---|---|---|
| WO | WO 2004-108418 A1 | 12/2004 |
| WO | WO 2005-057436 | 6/2005 |
| WO | WO 2007-024125 A1 | 3/2007 |
| WO | WO 2007-120840 A2 | 10/2007 |
| WO | WO 2007-124023 A2 | 11/2007 |
| WO | WO 2009-051701 A2 | 4/2009 |

OTHER PUBLICATIONS

Calvert P. Inkjet printing for materials and devices. Chem, Mater, 2001; 13(10): 3299-3305.

Boland T et al. Cell and organ printing 2: fusion of cell aggregates in three-dimensional gels, The Anatomical Record Part A. 2003; 272A: 497-502.

Pardo L et al, Characterization of patterned self-assembled monolayers and protein arrays generated by the Ink-jet method. Langmuir. 2003; 19(5): 1462-1466.

Wilson Jr WC and Boland T. Cell and organ printing 1: protein and cell printers, The Anatomical Record Part A. 2003; 272A: 491-496.

Xu T et al. Construction of high-density bacterial colony arrays and patterns by the Ink-jet method, Biotechnology and Bioengineering. Jan. 6, 2004; 85(1): 29-33.

Jakab K et al. Engineering biological structures of prescribed shape using self-assembling multicellular systems, PNAS. Mar. 2, 2004; 101(9): 2864-2869.

(Continued)

*Primary Examiner* — Janet Epps-Smith
(74) *Attorney, Agent, or Firm* — Myers Bigel & Sibley, P.A.

(57) ABSTRACT

Provided herein is an apparatus for printing cells which includes an electrospinning device and an inkjet printing device operatively associated therewith. Methods of making a biodegradable scaffold having cells seeded therein are also provided. Methods of forming microparticles containing one or more cells encapsulated by a substrate are also provided, as are methods of forming an array of said microparticles.

21 Claims, 8 Drawing Sheets

(56) References Cited

OTHER PUBLICATIONS

Li D and Xia Y. Electrospinning of nanofibers: reinventing the wheel? Advanced Materials. Jul. 19, 2004; 16(14): 1151-1170.

He M et al. Selective encapsulation of single cells and subcellular organelles into picoliter and femtoliter-volume droplets. Analytical Chemistry Mar. 15, 2005; 77(6): 1539-1544.

MacDonald et al., Collagen-carbon nanotube composite materials as scaffolds in tissue engineering. J. Blomed. Mater. Res. 2005; 74A(3): 489-496.

Xu T et al. Inkjet printing of viable mammalian cells. Biomaterials. 2005; 26: 93-99.

Boland T et al. Application of inkjet printing to tissue engineering, Biotechnol. J. 2006; 1: 910-917.

Park J and Moon J. Control of colloidal particle deposit patterns within picoliter droplets ejected by ink-jet printing. Langmuir. 2006; 22(8): 3506-3513.

Stankus JJ et al. Microintegrating smooth muscle cells into a biodegradable, elastomeric fiber matrix. Biomaterlals. 2006; 27: 735-744.

Xu T et al. Viability and electrophysiology of neural cell structures generated by the inkjet printing method. Biomaterials. 2006; 27: 3580-3588.

Tyson J. How inkjet printers work. Howstuffworks.com. Apr. 30, 2007: 3 pages.

International Search Report and Written Opinion, PCT/US2007/009161, mailed Oct. 24, 2007.

International Search Report and Written Opinion, PCT/US2009/000940, mailed Oct. 19, 2009.

Fullhase C et al. A novel hybrid printing system for the generation of organized bladder tissue. Journal of Urology. Apr. 27, 2009; 181(4)Suppl: 282-283.

* cited by examiner

INKJET PRINTING OF TISSUES AND CELLS

RELATED APPLICATIONS

This application is a divisional of and claims priority to U.S. patent application Ser. No. 14/185,090, filed Feb. 20, 2014, now allowed, which is a divisional of U.S. patent application Ser. No. 12/370,921, filed Feb. 13, 2009, now U.S. Pat. No. 8,691,274, which claims the benefit under 35 U.S.C. §119(e) of U.S. Provisional Patent Application Ser. No. 61/028,761, filed Feb. 14, 2008, the disclosure of each of which is incorporated herein by reference in its entirety.

FIELD OF THE INVENTION

The present invention concerns inkjet printing of viable cells and arrays of cells so produced.

BACKGROUND OF THE INVENTION

In the interdisciplinary field of tissue engineering, powerful new therapies are being developed to address structural and functional disorders of human health by utilizing living cells as engineering materials. In some areas of tissue engineering, researchers are creating two- and three-dimensional tissues and organs from combinations of cells in order to repair or replace diseased or damaged tissues.

Organ printing using inkjet printing is evolving to become more optimized by delivering multiple cell types and scaffolds to target specific regions. However, most current printing technologies are limited to hydrogel as the primary scaffold for tissue constructs. A major disadvantage of hydrogels is their low mechanical strength, which makes handling and in vivo application difficult, particularly for load-bearing implants. Alternative methods to create implants having enhanced mechanical properties are needed.

Inkjet printing technology is based on the rapid creation and release of liquid droplets, followed by their precise deposition on a substrate. Recently, this technology has generated increased interest in biomedical micro-fabrication, as it offers a practical and efficient method to dispense biological and/or material elements, including living cells (Boland et al., 2007, "Drop-on-demand printing of cells and materials for designer tissue constructs," Materials Science & Engineering C-Biomimetic and Supramolecular Systems, 27(3), pp. 372-376; Xu et al., 2006, "Viability and electrophysiology of neural cell structures generated by the inkjet printing method," Biomaterials, 27(19), pp. 3580-3588; Xu et al., 2005, "Inkjet printing of viable mammalian cells," Biomaterials, 26(1), pp. 93-99; Xu et al., 2004, "Construction of high-density bacterial colony arrays and patterns by the ink-jet method," Biotechnol Bioeng, 85(1), pp. 29-33).

The cell represents the basic unit of life and as such, it has become the focus of extensive research. Single-cell analysis is advantageous over conventional bulk cell methods as it allows complex and heterogeneous biological systems to be monitored at their most basic level (Shoemaker et al., 2007, "Multiple sampling in single-cell enzyme assays using capillary electrophoresis with laser-induced fluorescence detection," Anal Bioanal Chem, 387(1), pp. 13-15). In recent years, single-cell based analytical devices have been increasingly applied in a wide range of biomedical applications, such as single-cell assays (Lu et al., 2004, "Recent developments in single-cell analysis," Analytica Chimica Acta, 510(2), pp. 127-138), high throughput screening (Andersson et al., 2004, "Microtechnologies and nanotechnologies for single-cell analysis," Curr Opin Biotechnol, 15(1), pp. 44-49; Brehm-Stecher et al., 2004, "Single-cell microbiology: tools, technologies, and applications," Microbiol Mol Biol Rev, 68(3), pp. 538-559), single-cell protein libraries and gene expression (Fukuda et al., 2006, "Construction of a cultivation system of a yeast single cell in a cell chip microchamber," Biotechnology Progress, 22(4), pp. 944-948; Janicki et al., 2004, "From silencing to gene expression: Real-time analysis in single cells," Cell, 116(5), pp. 683-698), and miniature biosensors (Maruyama et al., 2005, "Immobilization of individual cells by local photo-polymerization on a chip," Analyst, 130(3), pp. 304-310). These devices usually require the use of appropriate carriers to deliver and manipulate single cells.

Recently, microparticles that contain individual living cells have been applied in single-cell analytical systems as effective carriers (He et al., 2005, "Selective encapsulation of single cells and subcellular organelles into picoliter- and femtolitervolume droplets," Anal Chem, 77(6), pp. 1539-1544). These particles provide easy handling of single cells and enhance detection efficiency (Huebner et al., 2007, "Quantitative detection of protein expression in single cells using droplet microfluidics," Chemical Communications(12), pp. 1218-1220). Moreover, these particles have been used as micro-reactors to enhance and accelerate chemical and biochemical screening (Song et al., 2006, "Reactions in droplets in microflulidic channels," Angewandte Chemie-International Edition, 45(44), pp. 7336-7356). This provides single cell analytical devices with new capabilities and improved detection efficiency (Taly et al., 2007, "Droplets as Microreactors for High-Throughput Biology," Chembiochem, 8(3), pp. 263-272).

Currently, single-cell microparticles are mainly fabricated using microfluidic based methods (He et al., 2005, "Selective encapsulation of single cells and subcellular organelles into picoliter- and femtolitervolume droplets," Anal Chem, 77(6), pp. 1539-1544; Huebner et al., 2007, "Quantitative detection of protein expression in single cells using droplet microfluidics," Chemical Communications(12), pp. 1218-1220; Song et al., 2006, "Reactions in droplets in microfluidic channels," Angewandte Chemie-International Edition, 45(44), pp. 7336-7356). However, these methods have some limitations. For example, micro-fluidic approaches are usually limited to specific geometries because they require laminar fluid flow to produce microparticles (Khademhosseini et al., 2004, "Layer-by-layer deposition of hyaluronic acid and poly-L-lysine for patterned cell cocultures," Biomaterials, 25(17), pp. 3583-3592). These methods can only create small quantities of particles, since there are a limited number of microchannels within these devices. Furthermore, the costly equipment, specialized material, and extensive expertise required for operation of these devices may further limit the use of these methods in single cell particle fabrication.

Thus, there is an acute need for more efficient approaches that can rapidly generate single cell microparticles with ease.

SUMMARY OF THE INVENTION

Provided herein is an apparatus for printing cells, including: (a) an electrospinning device having a high voltage power supply; and/or (b) an inkjet printing device operatively associated with the electrospinning device. In some embodiments, the apparatus includes a three dimensional plotter operatively connected with the electrospinning device and/or inkjet printing device. In some embodiments, the apparatus includes a controller operatively connected to the electrospinning device and/or inkjet printing device. In some embodiments, the high voltage supply is conductively isolated from, e.g., the controller and/or plotter (e.g., by optics or wireless communication).

Methods of making a biodegradable scaffold having cells seeded therein are also provided, including one or more of the steps of: (a) forming a biodegradable substrate by electrospinning; and then (b) printing viable cells on said substrate. In some embodiments, the forming step and the printing step are each performed two or more times in sequence to make a biodegradable scaffold having multiple layers.

Methods of treating a subject in need thereof are provided, including the step of implanting a biodegradable scaffold as described herein.

Methods of forming microparticles comprising, consisting of or consisting essentially of one or more cells encapsulated by a substrate are provided, including the step of printing a composition comprising the cells and the substrate (e.g., alginate).

Also provided are methods of forming an array of microparticles comprising one or more cells encapsulated by a substrate, including one or more of the steps of: providing an inkjet printing device, said device comprising at least one inkjet printer cartridge; loading a composition comprising said cells and said substrate into said printer cartridge; and printing said composition in an organized pattern.

The foregoing and other objects and aspects of the present invention are explained in greater detail in the drawings herein and the specification set forth below.

DETAILED DESCRIPTION OF THE PREFERRED EMBODIMENTS

Figure 1:
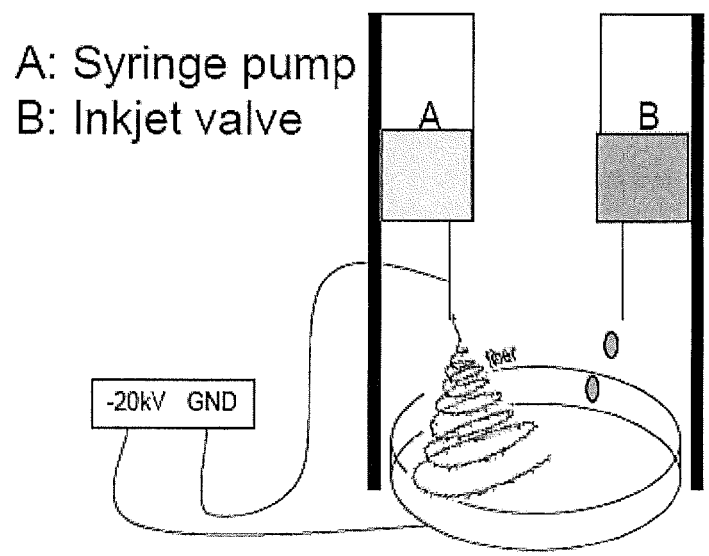
FIG. 1. Schematic diagram of dual inkjet and electrospinning apparatus used in Example 1. Polymer is loaded into the electrospinning syringe pump (A) with a ground charge attached to the polymer pump. The lower portion of the petri dish was charged with −20 kV. Chondrocytes suspended within a fibrin and collagen matrix were plated using an inkjet valve (B).

Provided herein and further described below are compositions, devices and methods useful for the printing of cells and tissues. The disclosures of all United States patent references cited herein are hereby incorporated by reference to the extent they are consistent with the disclosure set forth herein.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

A. Printing.

"Printing" as used herein refers to the delivery of individual droplets of cells and/or compositions with small volumes ranging from 0.5 to 500 picoLiters per droplet. In some embodiments, droplets have a volume ranging from 5 to 100 picoLiters per droplet. In other embodiments, droplets range from 10 to 75 picoLiters per droplet. Printing may be performed by, e.g., using standard printers with print heads that are modified as described herein. The "print head" is the device in an inkjet printer that sprays droplets (e.g., ink).

Methods and compositions for the inkjet printing of viable cells are known and described in, for example, U.S. Pat. No. 7,051,654 to Boland et al.; Wilson et al. (2003) The Anatomical Record Part A 272A: 491-496. The cells may also be printed by other means, such as the methods and compositions for forming three-dimensional structures by deposition of viable cells described in U.S. Pat. No. 6,986,739 to Warren et al.

Although not required, cells can typically be printed in the form of a "cell composition" that contains a liquid carrier for the cells. The cell composition can be in the form of a suspension, solution, or any suitable form. Examples of suitable liquid carriers include, but are not limited to, water, ionic buffer solutions (e.g., phosphate buffer solution, citrate buffer solution, etc.), liquid media (e.g., modified Eagle's medium ("MEM"), Hanks' Balanced Salts, etc.), and so forth. For instance, the use of a liquid carrier in the cell composition can ensure adequate hydration and minimize evaporation of the cells after printing. However, the probability of obtaining viable cells in any given printed drop also decreases with decreasing cell concentration. (T. Boland, US Patent Application Publication No. 20040237822 at para 48)

In some embodiments, cells/compositions are printed with a modified inkjet printer. Modifications may include, but are not limited to, means to control the temperature, humidity, shear force, speed of printing, and firing frequency, by modifications of, e.g., the printer driver software and/or the physical makeup of the printer. See, e.g., Pardo et al. (2003) *Langmuir* 19:1462-1466; U.S. Pat. No. 7,051,654 to Boland et al. Not every modification suggested in these references will be suitable to a given application, as will be appreciated by those skilled in the art. For example, in some embodiments, printers are not modified by using new gear mount pillars with closer tolerances by adding a horizontal support, changing the transistor in the circuit to one with higher amplification, and reentering the horizontal position encoder. Also, in some embodiments, printer software is not modified to lower the resistive voltages to avoid heating of the solutions above 37° C.

In some embodiments, the inkjet printing device includes a two-dimensional (X-Y) or three-dimensional (X-Y-Z) plotter (e.g., driven by the step motors). In some embodiments, the print head is equipped with a DC solenoid inkjet valve. In some embodiments, a reservoir for loading cell print suspension is connected to the inkjet valve. In some embodiments, the cell print suspension may be supplied from the reservoirs to the inkjet valve by air pressure. In some embodiments, the print head may be mounted over an X-Y-Z plotter to allow precise deposition of cells onto a scaffold. Positioning of the XYZ plotter under the print head may be controlled via a controller. In some embodiments, the controller acquires the positioning information from software loaded on a computer. In some embodiments, the software converts the image of the target to a four-byte protocol, which is used to activate specific inkjet valves and coordinate the X-Y-Z position.

In some embodiments, printers (e.g., the commercial printers HP695C and HP550C) may be modified as follows. The printer top cover may be removed and the sensor for the cover disabled. The paper feeding mechanism may be disabled to allow printing of cells onto solid substrates (e.g., scaffolds). The ink absorbing pads (which are on the right side of the HP695C and HP550C printers) may be removed (e.g., to avoid the pads contaminating the bottom of the print cartridges during the printing process). To offer the capability of the printer to print 3D constructs, a customized z-axis module with a controlled elevator chamber may be added.

In some embodiments, the inkjet printing device is a thermal bubble inkjet printer. In general, in a thermal bubble inkjet printer, resistors create heat in the print head, which vaporizes ink to create a bubble. As the bubble expands, some of the ink is pushed out of a nozzle onto the paper. A vacuum is created when the bubble collapses, which pulls more ink into the print head from the cartridge. In the present invention, the ink is replaced with, e.g., cells and/or compositions of interest (e.g., cells in a liquid carrier), and the paper is replaced with a suitable substrate, e.g., an agar or collagen coated substrate, or a suitable scaffold. See, e.g., U.S. Pat. No. 6,537,567 to Niklasen et al.

In other embodiments, cells are printed using a piezoelectric crystal vibration print head. In general, a piezoelectric crystal receives an electric charge that causes it to vibrate, forcing ink out of the nozzle, and pulling more ink into the reservoir. In the present invention, the ink is replaced with, e.g., cells and/or a compositions of interest. Compared with the thermal inkjet printing, the piezo-based inkjet printing usually requires more power and higher vibration frequencies. Typical commercial piezo-printers use frequencies up to 30 kHz and power sources ranging from 12 to 100 Watts. Therefore, in some embodiments a piezoelectric crystal vibration print head is used, with a vibrating frequency of 1, 5, 10 or 15, to 20, 25, 30, or 35 or more kHz, and power sources from 5, 10, 20, 50, 100, 120, or 150, to 200, 250, 300, 350, or 375 or more Watts.

In some embodiments, the print head nozzles are each independently between 0.05 and 200 μm in diameter, or between 0.5 and 100 μm in diameter, or between 10 and 70 μM, or between 20 and 60 μm in diameter. In further embodiments, the nozzles are each independently about 40 or 50 μm in diameter. A plurality of nozzles with the same or different diameters may be provided. Though in some embodiments the nozzles have a circular opening, other suitable shapes may be used, e.g., oval, square, rectangle, etc., without departing from the spirit of the invention.

As a general guide, eukaryotic animal cells and plant cells are typically from 10 to 100 μm, and prokaryotic cells are typically from 0.1 to 10 μm in diameter. Before printing, in some embodiments the cells may be enzymatically dissociated, e.g., from culture plates or explant tissues. Upon enzymatic treatment, the cells typically to shrink to smaller balls. As a general guide, after enzymatic treatment animal cells are typically from several micrometers to 30 micrometers. For example, after trypsin treatment, cells of a porcine aortal endothelial cell line (PAEC cells) are about 10-20 μm.

In some embodiments, the cells/compositions are formulated to provide an encapsulated form upon printing. The encapsulation of cells in permeable capsules are known and described in, for example, U.S. Pat. No. 6,783,964. For example, the cells may be encapsulated in a microcapsule of from 50 or 100 μm to 1 or 2 mm in diameter that includes an internal cell-containing core of polysaccharide gum surrounded by a semipermeable membrane; a microcapsule that includes alginate in combination with polylysine, polyornithine, and combinations thereof. Other suitable encapsulating materials include, but are not limited to, those described in U.S. Pat. No. 5,702,444.

"Encapsulated" cells are cells or small clusters of cells or tissue that are surrounded by a selective membrane laminate that allows passage of oxygen and other required metabolites, releases certain cell secretions (e.g., insulin), but limits the transport of the larger agents of the host's immune system to prevent immune rejection. Encapsulation may be useful for, e.g., implanting and/or injecting cells or tissues containing living xenogeneic or allogeneic cells while reducing the risk of immune rejection in a host. This may be useful, e.g., to treat diseases due to inadequate or loss or secretory cell function, or ailments that would benefit from the addition of certain secretory cells, e.g., acute liver failure, type I diabetes, chronic pain, Parkinson's disease, etc. Other uses of encapsulated cells as described herein include, but are not limited to, single cell analysis, high throughput drug screening, and stem cell differentiation at the single cell level.

"Microencapsulation" of cells is where one, two, three or several cells are encapsulated. The microencapsulated cells may be referred to as "microparticles." In some embodiments, each membrane encapsulates 10 cells or less, preferably 5 cells or less, of at least 50, 70, 80, 90 or 95% or more of the printed cells.

In some embodiments, three-dimensional arrays are formed. Three-dimensional cell arrays are commonly used in tissue engineering and biotechnology for in vitro and in vivo cell culture. In general, a three-dimensional array is one which includes two or more layers separately applied to a substrate, with subsequent layers applied to the top surface of previous layers. The layers can, in one embodiment, fuse or otherwise combine following application or, alternatively, remain substantially separate and divided following application to the substrate. Three-dimensional arrays may be formed in a variety of ways in accordance with the present invention. For example, in one embodiment, three-dimensional arrays may be formed by printing multiple layers onto the substrate.

The thickness of a printed layer (e.g., cell layer, support layer, etc.) may generally vary depending on the desired application. For example, in some embodiments, the thickness of a layer containing cells is from about 2 micrometers to about 3 millimeters, and in some embodiments, from about 20 micrometers to about 100 micrometers. Further, as indicated above, support compounds, such as gels, are often used to facilitate the survival of printed cells.

When printing certain types of two-dimensional or three-dimensional arrays, it is sometimes desired that any subsequent cell growth is substantially limited to a predefined region. Thus, to inhibit cell growth outside of this predefined region, compounds may be printed or otherwise applied to the substrate that inhibit cell growth and thus form a boundary for the printed pattern. Some examples of suitable compounds for this purpose include, but are not limited to, agarose, poly (isopropyl N-polyacrylamide) gels, and so forth. In one embodiment, for instance, this "boundary technique" may be employed to form a multi-layered, three-dimensional tube of cells, such as blood vessels. For example, a cell suspension may be mixed with a first gel ("Gel A") in one nozzle, while a second gel ("Gel B") is loaded into another nozzle. Gel A induces cell attachment and growth, while Gel B inhibits cell growth. To form a tube, Gel A and the cell suspension are printed in a circular pattern with a diameter and width corresponding to the diameter and wall thickness of the tube, e.g., from about 3 to about 10 millimeters in diameter and from about 0.5 to about 3 millimeters in wall thickness. The inner and outer patterns are lined by Gel B defining the borders of the cell growth. For example, a syringe containing Gel A and "CHO" cells and a syringe containing Gel B may be connected to the nozzle. Gel B is printed first and allowed to cool for about 1 to 5 minutes. Gel A and CHO cells are then printed on the agarose substrate. This process may be repeated for each layer.

The present invention includes the printing of tissues by the appropriate combination of cell and support material, or two or three or more different cell types typically found in a common tissue, preferably along with appropriate support compound or compounds, and optionally with one or more appropriate growth factors. Cells, support compounds, and growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degradable support material), and some of the ingredients may be printed in the form of a second pattern (e.g., cells in a pattern different from the support, or two different cell types in a different pattern). Again, the particular combination and manner of printing will depend upon the particular tissue construct desired.

B. Cells.

Any type of cell may be printed using the methods herein, including prokaryotic and eukaryotic cells. Examples of eukaryotic cells that may be printed using the methods herein include, but are not limited to, mammalian cells, including stem cells, progenitor cells and differentiated cells, without limitation. Stem cells have the ability to replicate through numerous population doublings (e.g., at least 60-80), in some cases essentially indefinitely, and also have the ability to differentiate into multiple cell types (e.g., is pluripotent or multipotent). It is also possible for cells to be transfected with a compound of interest that results in the cells becoming immortalized (i.e., able to double more than 50 times). For example, it has been reported that mammalian cell transfection with telomerase reverse transcriptase (hTERT) can immortalize neural progenitor cells (See U.S. Pat. No. 7,150,989 to Goldman et al.).

"Embryonic stem cell" as used herein refers to a cell that is derived from the inner cell mass of a blastocyst and that is pluripotent.

"Amniotic fluid stem cell" as used herein refers to a cell, or progeny of a cell, that (a) is found in, or is collected from, mammalian amniotic fluid, mammalian chorionic villus, and/or mammalian placental tissue, or any other suitable tissue or fluid from a mammalian donor, (b) is pluripotent; (c) has substantial proliferative potential, (d) optionally, but preferably, does not require feeder cell layers to grow in vitro, and/or (e) optionally, but preferably, specifically binds c-kit antibodies (particularly at the time of collection, as the ability of the cells to bind c-kit antibodies may be lost over time as the cells are grown in vitro).

"Pluripotent" as used herein refers to a cell that has complete differentiation versatility, e.g., the capacity to grow into any of the animal's cell types. A pluripotent cell can be self-renewing, and can remain dormant or quiescent with a tissue. Unlike a totipotent cell (e.g., a fertilized, diploid egg cell) a pluripotent cell cannot usually form a new blastocyst.

"Multipotent" as used herein refers to a cell that has the capacity to grow into any of a subset of the corresponding animal cell types. Unlike a pluripotent cell, a multipotent cell does not have the capacity to form all of the cell types of the corresponding animal.

Cells may be syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the subject to be treated) and isogeneic (i.e., a genetically identical but different subject, e.g., from an identical twin). Cells may be obtained from, e.g., a donor (either living or cadaveric) or derived from an established cell strain or cell line. For example, cells may be harvested from a donor (e.g., a potential recipient of a bioscaffold graft) using standard biopsy techniques known in the art.

According to some embodiments, at least a portion of the cells are viable after they are printed. "Viable cells" includes cells that adhere to a culture dish or other substrate and/or are capable of survival (e.g., proliferation). In some embodiments, at least 30, 40 or 50% of the total cells loaded are viable, and in further embodiments at least 60, 70, 80, or 90% or more of the total cells loaded are viable after printing. Cell viability may be measured by any conventional means, e.g., the MTS assay, and at a reasonable time after printing, e.g., 1 day after printing completion. Viability is measured upon incubation under conditions known in the art to be optimal for survival of the certain cells types present. For example, many eukaryotic cell types are typically incubated in a suitable medium at 5% carbon dioxide (95% atmospheric air) and 37 degrees Celsius.

Various mechanisms may be employed to facilitate the survival of the cells during and/or after printing. Specifically, compounds may be utilized that support the printed cells by providing hydration, nutrients, and/or structural support. These compounds may be applied to the substrate using conventional techniques, such as manually, in a wash or bath, through vapor deposition (e.g., physical or chemical vapor deposition), etc. These compounds may also be combined with the cells and/or compositions before and/or during printing, or may be printed or otherwise applied to the substrate (e.g., coated) as a separate layer beneath, above, and/or between cell layers. For example, one such support compound is a gel having a viscosity that is low enough under the printing conditions to pass through the nozzle of the print head, and that can gel to a stable shape during and/or after printing. Such viscosities are typically within the range of from about 0.5 to about 50 centipoise, in some embodiments from about 1 to about 20 centipoise, and in some embodiments, from about 1 to about 10 centipoise. Some examples of suitable gels that may be used in the present invention include, but are not limited to, agars, collagen, hydrogels, etc.

Another polymer used for hydrogels is alginate, a natural polysaccharide extracted from seaweed. One feature of alginate solutions is their gelling properties in the presence of divalent cations (e.g., $Mg^{++}$, $Ca^{++}$, $Sr^{++}$, $Ba^{++}$).

Besides gels, other support compounds may also be utilized in the present invention. Extracellular matrix analogs, for example, may be combined with support gels to optimize or functionalize the gel. In some embodiments, one or more growth factors may also be introduced in the printed arrays. For example, slow release microspheres that contain one or more growth factors in various concentrations and sequences may be combined with the cells and/or composition. Other suitable support compounds might include those that aid in avoiding apoptosis and necrosis of the developing structures. For example, survival factors (e.g., basic fibroblast growth factor) may be added. In addition, transient genetic modifications of cells having antiapoptotic (e.g., bcl-2 and telomerase) and/or blocking pathways may be included in compositions printed. Adhesives may also be utilized to assist in the survival of the cells after printing. For instance, soft tissue adhesives, such a cyanoacrylate esters, fibrin sealant, and/or gelatin-resorcinol-formaldehyde glues, may be utilized to inhibit nascent constructs from being washed off or moved following the printing of a layer. In addition, adhesives, such as arginine-glycine-aspartic acid (RGD) ligands, may enhance the adhesion of cells to a gelling polymer or other support compound. Extracellular proteins, extracellular protein analogs, etc., may also be utilized.

"Growth factor" may be any naturally occurring or synthetic growth factor, including combinations thereof, suitable for the particular tissue or array being printed. Numerous growth factors are known. Examples include, but are not limited to, insulin-like growth factor (e.g., IGF-1), transforming growth factor-beta (TGF-beta), bone-morphogenetic protein, fibroblast growth factor, platelet derived growth factor (PDGF), vascular endothelial growth factor (VEGF), connective tissue growth factor (CTGF), basic fibroblast growth factor (bFGF), epidermal growth factor, fibroblast growth factor (FGF) (numbers 1, 2 and 3), osteopontin, bone morphogenetic protein-2, growth hormones such as somatotropin, cellular attractants and attachment agents, etc., and mixtures thereof. See, e.g., U.S. Pat. Nos. 7,019,192; 6,995,013; and 6,923,833. For example, growth factor proteins may be provided in the printed composition and/or encoded by plasmids transfected into printed cells.

In some embodiments, cells, compositions, support compounds, and/or growth factors may be printed from separate nozzles or through the same nozzle in a common composition, depending upon the particular tissue (or tissue substitute) being formed. Printing may be simultaneous, sequential, or any combination thereof. Some of the ingredients may be printed in the form of a first pattern (e.g., an erodable or degradable support material), and some of the ingredients may be printed in the form of a second pattern (e.g., cells in a pattern different from the support, or two different cell types in a different pattern). The particular combination and manner of printing will depend upon the particular tissue being printed.

In some embodiments, cells/compositions are printed onto a substrate, e.g., a biocompatible scaffold, which may be subsequently implanted into a subject in need thereof. In other embodiments, cells/compositions of interest are directly printed in vivo onto living tissues in the body, with or without prior substrate application (e.g., a layer of fibrin) in which the cells may attach.

"Isolated" as used herein signifies that the cells are placed into conditions other than their natural environment. Tissue or cells are "harvested" when initially isolated from a subject, e.g., a primary explant.

The "primary culture" is the first culture to become established after seeding disaggregated cells or primary explants into a culture vessel. "Expanding" or "expansion" as used herein refers to an increase in number of viable cells. Expanding may be accomplished by, e.g., "growing" the cells through one or more cell cycles, wherein at least a portion of the cells divide to produce additional cells. "Growing" as used herein includes the culture of cells such that the cells remain viable, and may or may not include expansion and/or differentiation of the cells.

"Passaged in vitro" or "passaged" refers to the transfer or subculture of a cell culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics (e.g., the ability to express a certain protein or marker).

"Express" or "expression" of a protein or other biological marker means that a gene encoding the same of a precursor thereof is transcribed, and preferably, translated. Typically, according to the present invention, expression of a coding region of a gene will result in production of the encoded polypeptide, such that the cell is "positive" for that protein or other downstream biological marker.

"Cartilage cells" include those cells normally found in cartilage, which cells include chondrocytes. "Chondrocytes" produce and maintain the extracellular matrix of cartilage, by, e.g., producing collagen and proteoglycans. Cartilage is a highly specialized connective tissue found throughout the body, and its primary function is to provide structural support for surrounding tissues (e.g., in the ear and nose) or to cushion (e.g., in the trachea and articular joints). Types of cartilage include hyaline cartilage (articular joints, nose, trachea, intervertebral disks (NP), vertebral end plates), elastic cartilage (tendon insertion site, ligament insertion site, meniscus, intervertebral disks (AP)), costochondral cartilage (rib, growth plate), and fibrocartilage (ear). The loss of cartilage in a subject can be problematic, as it has a very limited repair capacity. "Mesenchymal stem cells" or "MSCs" are progenitors of chondrocytes. MSCs can also differentiate into osteoblasts. Cartilage cells/tissues produced by the processes described herein are useful for, among other things, implantation into a subject to treat cartilage injury or disease.

"Bone cells" include those cells normally found in bone, and include osteoblasts, osteoclasts, osteocytes, and any combination thereof. Bone cells/tissues produced by the processes described herein are useful for, among other things, implantation into a subject to treat bone fractures or defects, and/or promote bone healing.

"Muscle cells" include those cells normally found in muscle tissue, including smooth muscle cells, cardiac muscle cells, skeletal muscle cells, and any combination thereof. Muscle cells/tissues produced by the processes described herein are useful for, among other things, implantation into a subject to treat muscle injuries or defects, and/or promote muscle healing.

"Skin cells" include those cells normally found in skin, and include epidermal cells (e.g., keratinocytes, melanocytes, Merkel cells, Langerhan cells, etc., and any combination thereof) and dermal cells (e.g., fibroblasts, adipocytes, mast cells, macrophages, and any combination thereof). Skin tissue produced by the process of the present invention is useful for implantation into or on a subject to, for example, treat burns, and other wounds such as incisions, lacerations, and crush injuries (e.g., postsurgical wounds, and posttraumatic wounds, venous leg ulcers, diabetic foot ulcers, etc.)

"Pancreatic cells" include those cells normally found in the pancreas, and include pancreatic islet cells, e.g., glucagon-synthesizing A ($\alpha$) cells, insulin-producing B ($\beta$) cells, D ($\delta$) cells, etc., and any combination thereof. Pancreatic islet tissue produced by the processes described herein is useful for, among other things, implantation into a subject to treat diabetes (including type I and type II diabetes).

"Kidney cells" include those cells normally found in the kidney, and include interstitial cells (e.g., interstitial peritubular cells which secrete erythropoietin), endothelial cells, etc., or any combination thereof.

"Nervous system cells" or "nerve cells" include those cells normally found in the central and/or peripheral nervous system, including neuronal cells (e.g., cortical neurons, hippocampal neurons, dopaminergic neurons, cholinergic neurons, adrenergic neurons, noradrenergic neurons, etc., including any combination thereof), and glial cells (e.g., neuroglia, astrocytes, oligodendrocytes, Schwann cells, etc., including any combination thereof). Nerve cells produced by the processes described herein is useful, among other things, for implantation into a subject to treat nerve injury or degenerative diseases such as Parkinson's disease and Alzheimer's disease.

"Liver cells" include those cells normally found in the liver, and include hepatoblasts, hepatocytes, hepatic stellate cells, Kupffer cells, sinusoidal endothelial cells, etc., including any combination thereof. Livers cells produced by the processes described herein is useful, among other things, for implantation into a subject to treat acute or chronic liver disease.

In some embodiments stem cells are printed onto substrates by inkjet printing. Stem cells may be printed alone (typically in combination with a support compound or compounds) or in combination with one or more additional cells (e.g., in a combination selected to produce a tissue as described above). In some embodiments, stem cells are differentiated into cells of interest.

"Differentiation" and "differentiating" as used herein include (a) treatment of the cells to induce differentiation and completion of differentiation of the cells in response to such treatment, both prior to printing on a substrate, (b) treatment of the cells to induce differentiation, then printing of the cells on a substrate, and then differentiation of the cells in response to such treatment after they have been printed, (c) printing of the cells, simultaneously or sequentially, with a differentiation factor(s) that induces differentiation after the cells have been printed, (d) contacting the cells after printing to differentiation factors or media, etc., and combinations of all of the foregoing. In some embodiments differentiation may be modulated or delayed by contacting an appropriate factor or factors to the cell in like manner as described above. In some embodiments appropriate differentiation factors are one or more of the growth factors described above. Differentiation and modulation of differentiation can be carried out in accordance with known techniques, e.g., as described in U.S. Pat. No. 6,589,728, or U.S. Patent Application Publication Nos.: 2006006018 (endogenous repair factor production promoters); 20060013804 (modulation of stem cell differentiation by modulation of caspase-3 activity); 20050266553 (methods of regulating differentiation in stem cells); 20050227353 (methods of inducing differentiation of stem cells); 20050202428 (pluripotent stem cells); 20050153941 (cell differentiation inhibiting agent, cell culture method using the same, culture medium, and cultured cell line); 20050131212 (neural regeneration peptides and methods for their use in treatment of brain damage); 20040241856 (methods and compositions for modulating stem cells); 20040214319 (methods of regulating differentiation in stem cells); 20040161412 (cell-based VEGF delivery); 20040115810 (stem cell differentiation-inducing promoter); 20040053869 (stem cell differentiation); or variations of the above or below that will be apparent to those skilled in the art.

Generally, when cells of the invention are used for treating a subject, e.g., encapsulated cells, the cells are formulated into a pharmaceutical composition containing the cells in admixture with a pharmaceutically acceptable vehicle or carrier. Such formulations can be prepared using techniques well known in the art. See, e.g., U.S. Patent Application 2003/0180289; Remington: *The Science and Practice of Pharmacy*, Alfonso R. Gennaro, editor, 20th ed. Lippincott Williams & Wilkins: Philadelphia, Pa., 2000. In the manufacture of a pharmaceutical formulation according to the invention, the cells are typically admixed with, inter alia, an acceptable carrier. The carrier must, of course, be acceptable in the sense of being compatible with any other ingredients in the formulation and must not be deleterious to the patient. The carrier may be a solid or a liquid, or both (e.g., hydrogels), and can be formulated with the cells as a unit-dose formulation. In one embodiment the cells are provided as a suspension in the carrier to reduce clumping of the cells.

"Implant" refers to a product configured to repair, augment or replace (at least a portion of) a natural tissue of a subject, e.g., for veterinary or medical (human) applications. The term "implantable" means the device can be inserted, embedded, grafted or otherwise chronically attached or placed on or in a patient. Implants include, but are not limited to, a "scaffold" or "bioscaffold" (which may or may not further comprise cells seeded onto the scaffold or bioscaffold).

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes.

"Treat" refers to any type of treatment that imparts a benefit to a subject, e.g., a patient afflicted with a trauma or a disease. For example, arthritis is a disease that affects cartilage. Treating includes actions taken and actions refrained from being taken for the purpose of improving the condition of the patient (e.g., the relief of one or more symptoms), delay in the onset or progression of the disease, etc. In some embodiments, treating includes reconstructing cartilage tissue (e.g., where such tissue has been damaged or lost by injury or disease) by implanting a scaffold into a subject in need thereof. Scaffolds may be implanted, e.g., at or adjacent to the site of injury, and/or at another site in the body of a subject that would impart a benefit to the subject, as would be appreciated by one of skill in the art.

C. Scaffolds.

"Scaffold" or "bioscaffold" refers to an array of natural and/or synthetic matrix molecules to which cells or fibers can attach. The fibers may include extracellular matrix molecules or components, such as elastin, elastic strands or peptides, fibrin, collagen, proteoglycans, hyaluronan or hyaluronan oligomers, synthetic fibers or fibrils, or bioactive hydrogels, microparticles, beads, liposomes, or vesicles. Scaffolds may further include extracellular matrix components, such as elastin, elastin-like or elastin-mimetic peptides, fibrin, proteoglycans, commercially available matrix or matrix-substitutes such as Matrigel™ matrix (BD Biosciences, San Jose, Calif., USA), collagen of any type, synthetic fibers or fibrils, and/or hydrogels.

Collagens are found throughout the body, and are of at least 12 types (type I-XII). As an example, the primary type of collagen found in articular cartilage is type II, followed by type IX and type XI.

A "biodegradable scaffold," "biodegradable mesh" or "biodegradable matrix" is a scaffold having materials capable of being degraded and/or absorbed by a subject's body. Desirably, the scaffold or matrix is porous to allow for cell deposition both on and in the pores of the matrix, and, in certain embodiments, is shaped. Such formulations can be prepared by supplying at least one cell population to a biodegradable scaffold to seed the cell population on and/or into the scaffold. In some embodiments, the seeded scaffold is then implanted in the body of the recipient subject, where the organized cell populations facilitate the formation of functional tissue structures.

Biodegradable materials that may be used include, e.g., natural polymers, such as collagen and elastin, and/or synthetic polymers, which can be degraded, e.g., by hydrolysis, at a controlled rate and are reabsorbed. Examples of other suitable materials are provided in U.S. Pat. No. 7,186,554, which is incorporated by reference herein.

Examples of biodegradable synthetic polymers include, but are not limited to, poly(lactide)s, poly(glycolide)s, poly(lactide-co-glycolide)s, poly(lactic acid)s, poly(glycolic acid)s, poly(lactic acid-co-glycolic acid)s, poly(caprolactone)s, polycarbonates, polyesteramides, polyanhydrides, poly(amino acid)s, poly(ortho ester)s, polycyanoacrylates, polyamides, polyacetals, poly(ether ester)s, copolymers of poly(ethylene glycol)s and poly(ortho ester)s, poly(dioxanone)s, poly(alkylene alkylate)s, biodegradable polyurethanes, as well as copolymers thereof. See, e.g., U.S. Pat. No. 7,097,857, which is incorporated by reference herein. Any polymer or copolymer may be combined or blended by methods known in the art.

For example, poly(lactide)s include, but are not limited to, poly(lactide) (also known as polylactic acid, or PLA) such as poly($_L$-lactide) (PLLA), poly($_{D,L}$-lactide) (PDLLA), and copolymers thereof. Copolymers of poly(lactide) include, but are not limited to, poly(lactide-co-glycolide) (PLGA), which is a copolymer of PLA with polyglycolide (PGA) (e.g., poly($_{D,L}$-lactide-co-glycolide)); and poly(lactide-co-caprolactone) (PLCL), which is a copolymer of PLA with poly(caprolactone) (PCL).

Examples of poly(caprolactone)s include, but are not limited to, poly($\epsilon$-caprolactone). Copolymers of PCL include, but are not limited to, poly(lactide-co-caprolactone) (PLCL), etc.

In some embodiments, cells and/or substrates may be oriented with respect to one or more axes. "Oriented" cells and/or substrates typically have one (or more) axis of orientation (e.g., longitudinal axis), which may be in any desired direction within the region of interest. It will be appreciated that "orienting" as used herein may include partial or total orientation, so long as a sufficient increase in organization is achieved to produce the effect or benefit intended for the particular implementation of the method described herein. For example, fibers and/or cells may be oriented along a longitudinal axis such that greater than 70, 80, 90, or 95% or more of the fibers and/or cells are at an angle of 50, 40, 30, 20, or 10 degrees or less from the reference axis in any direction.

"Anisotropic" means that the physical properties (e.g., elasticity, tensile strength, elongation at break, etc.) of a material (e.g., myotube, scaffold, etc.) are different depending upon the direction of action (e.g., stretch or strain), as opposed to "isotropic," in which the properties of a material are identical in all directions. For example, an anisotropic cell substrate may have a greater ultimate tensile strength along one axis (e.g., the longitudinal axis) than along an axis perpendicular to the axis (e.g., by 0, 1 or 2 to 4, 5, 6 or more MPa measured under wet condition at room temperature). The elongation at break may be smaller along one axis (e.g., the longitudinal axis) than along an axis perpendicular to the axis (e.g., by 10, 20, 30 or 40 to 50, 60, 70 or 80% or more). The peak of a stress curve (MPa) may be reached at a lower strain (%) along one axis (e.g., the longitudinal axis) as compared to an axis perpendicular to the axis.

In some embodiments, the biodegradable scaffold can be "shaped" using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape that resembles the final form. Next, a solvent is used to dissolve away one of the components, resulting in pore formation (see U.S. Pat. No. 5,514, 378). In nucleation, thin films in the shape of a reconstructive graft are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a reconstructive graft structure with uniform pore sizes. These shaping techniques may be employed in combination. For example, a biodegradable matrix can be weaved, compression molded and also glued. Furthermore, different polymeric materials shaped by different processes may be joined together to form a composite shape. The composite shape can be a laminar structure. For example, a polymeric matrix can be attached to one or more polymeric matrixes to form a multilayer polymeric matrix structure. The attachment can be performed by gluing with a liquid polymer or by suturing. In addition, the polymeric matrix can be formed as a solid block and shaped by laser or other standard machining techniques to its desired final form. Laser shaping refers to the process of removing materials using a laser.

The biodegradable scaffold can be treated with additives or drugs prior to implantation (before or after it is seeded with cells), e.g., to promote the formation of new tissue after implantation. Thus, for example, growth factors, cytokines, extracellular matrix components, and/or other bioactive materials can be added to the biodegradable scaffold to promote graft healing and the formation of new tissue. Such additives will in generally be selected according to the tissue or organ being reconstructed or augmented, to ensure that appropriate new tissue is formed in the engrafted organ or tissue. For examples of such additives for use in promoting bone healing, see, e.g., Kirker-Head (1995) *Vet. Surg.* 24 (5):408-19.

D. Electrospinning.

In some embodiments, scaffolds are formed by electrospinning. "Electrospinning" is a fiber spinning technique driven by a high voltage electrostatic field using a polymer solution that produces fibers with diameters ranging from several micrometers down to 100 nm or less. In some embodiments, fibers have an average diameter from 10, 100, or 200 nm to 400, 500, 750 or 1000 nm. The nano-scaled structure of the electrospun scaffolds can support cell adhesion and guide their behavior. Moreover, the composition, structure, and mechanical properties of biomaterials can be controlled. See, e.g., Li et al., "Electrospinning of Nanofibers: Reinventing the Wheel?" Advanced Materials (2004) vol. 16, no. 4, pp. 1151-1170. See also U.S. Pat. Nos. 7,326,043; 7,323,425; 7,172,765, each of which is incorporated by reference herein.

To avoid the potential adverse effect caused by static discharge of high voltage on other devices (e.g., a controller), in some embodiments an apparatus useful for electrospinning includes means for conductive isolation of the high voltage.

In some embodiments, a device is provided that is configured for both electrospinning and inkjet printing. In some embodiments, the inkjet printing platform includes an XYZ plotter driven by the step motors and the print head equipped with a DC solenoid inkjet valve. The print head may be mounted over a XYZ plotter platform to allow precise deposition of cells onto a scaffold generated by electrospinning. In some embodiments, positioning the XYZ plotter under the print head is controlled via a controller, which acquires the positioning information from software loaded on a computer. This software converts the image of the target to a special four byte protocol, which is used to activate specific inkjet valve and coordinate X-Y-Z position. In some embodiments, scaffolds are spun and/or cells are printed directly into a suitable liquid (e.g., media).

According to some embodiments, the electrospinning apparatus is used to generate polymeric fiber-based scaffolds. In some embodiments, an electrospinning head is also mounted over the XYZ plotter (e.g., in tandem with the inkjet head). In some embodiments, the high voltage power supply, used to provide a high voltage field for electrospinning, is modulated by the same controller as the XYZ plotter.

In order to avoid the potential adverse effects caused by static discharge of high voltage on the logic circuitry of the customized controller, according to some embodiments the controller is conductively isolated from the high voltage power supply.

In some embodiments, "conductive isolation" may include the use of wireless communication. Wireless communication includes, but is not limited to, radio frequency communications including, for example, a near field communication (NFC) protocol, Bluetooth, and/or Wifi, among others. Some embodiments may include one or more transceivers coupled to the electro-spinning print head and/or the controller.

In some embodiments, conductive isolation may include may include fiber optics communication. Fiber optics may use light transmission to receive and/or send the data between the control system and the high voltage supply. Some embodiments may include optical encoders and/or decoders.

In some embodiments, the scaffold is created "in sequence" layer-by-layer, with an electrospun layer (A), then a printed layer (B) in series, such as:

ABABABABABABABA

Each layer may include one or more individual layers of the same composition, e.g., layer A includes more than one layer of electrospun material, layer B includes more than one layer of an inkjet printed composition, etc. For example, a layer "B" may include individual layers of different cell types that together form a tissue.

The use of a layer-by-layer arrangement according to some embodiments can provide adequate mechanical properties for implanting a scaffold construct into a subject. For example, according to some embodiments, the scaffold is capable of being sutured as part of implantation surgery. Non-woven electrospun fibers can be spun to have controlled architectures, including aligned fibers, fibers having certain angles with respect to one or more axes, etc., as needed to more precisely mimic the natural environment of the tissue being created.

The present invention is explained in greater detail in the following non-limiting examples.

Example 1

Printing Cartilage Constructs Using a Hybrid Printing Device

Figure 2:
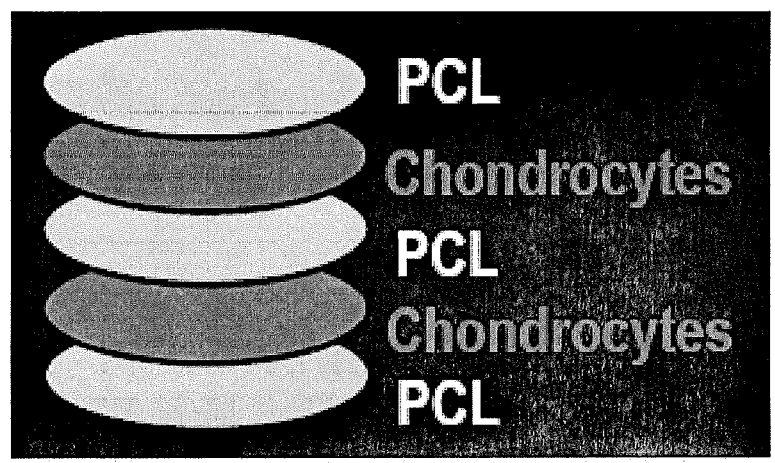
FIG. 2. Schematic diagram of layer-by-layer arrangement of PCL and chondrocytes created by electrospinning and inkjet printing in series.

To demonstrate the feasibility of generating structured cartilage constructs using a combination of electrospinning and inkjet printing, a layer-by-layer electrospun PCL and inkjet printed chondrocyte scaffold was created (FIG. 1 and FIG. 2).

Figure 3:
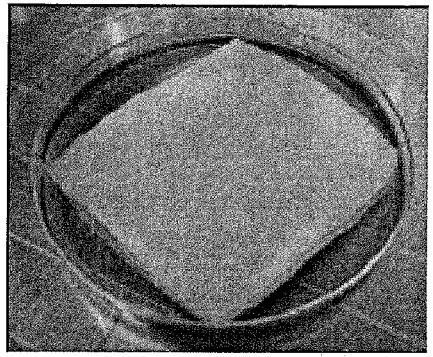
FIG. 3. Photograph of PCL-chondrocyte tissue construct formed by layer-by-layer arrangement.
Figure 4:
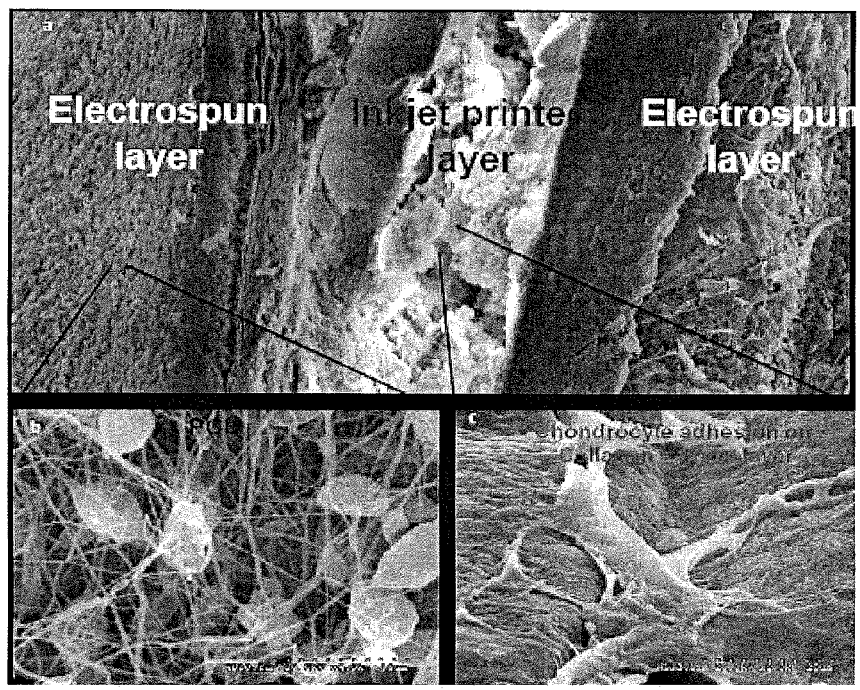
FIG. 4. SEM microscopy images of layered cartilage constructs, showing the inkjet printed layer situated between two electrospun layers (top panel a, 500×), and higher magnification of the electrospun PCL layer (bottom left panel b, 4000×) and inkjet printed chondrocyte, collagen and fibrin layer (bottom right panel c, 4000×).
Figure 5:
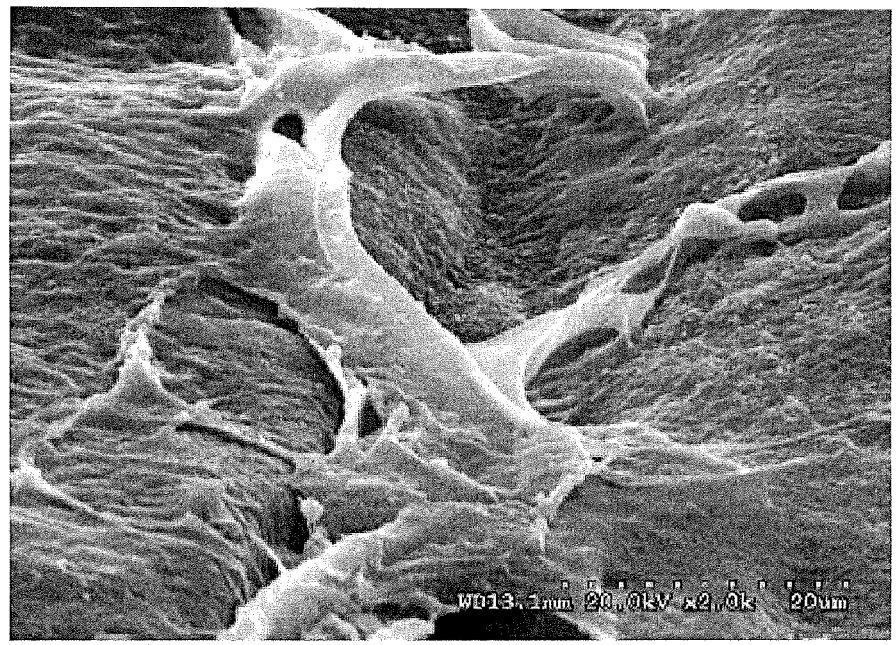
FIG. 5. An image of the inkjet printed layer reveals that printed chondrocytes attached onto the collagen/fibrin layer and produce elastic cartilage.

Electrospinning was first used to fabricate the PCL scaffold layer with polymeric nanofibers. Then the inkjet print head laid down rabbit elastic chondrocytes with the fibrin hydrogels on the electro-spun layer. By alternately applying electrospinning and inkjet printing, a 3D cartilage construct containing multi-layers of cells and scaffolds was generated (FIG. 3). The multi-layered structures of the constructs were observed under SEM examination (FIG. 4). Printed chondrocytes attached to the collagen/elastin within the layer (FIG. 5).

Figure 6:
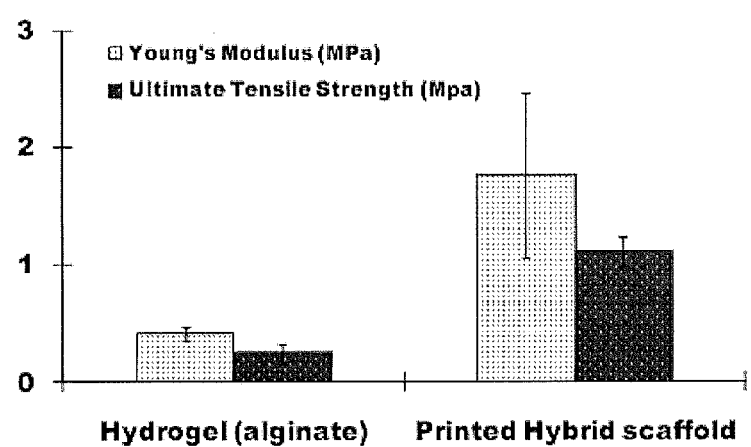
FIG. 6. Testing of mechanical properties revealed that hybrid constructs showed higher Young's modulus and UTS than printed alginate scaffolds.
Figure 7:
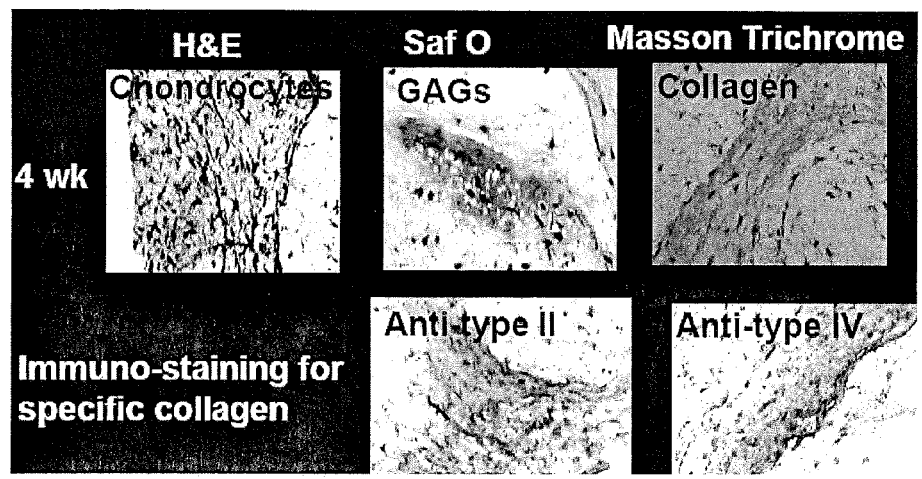
FIG. 7. Histology showed the production of cartilage-specific extracellular matrix (ECM) by the presence of cells, GAGs, and Type II & IV collagen within the printed constructs.
Figure 8:
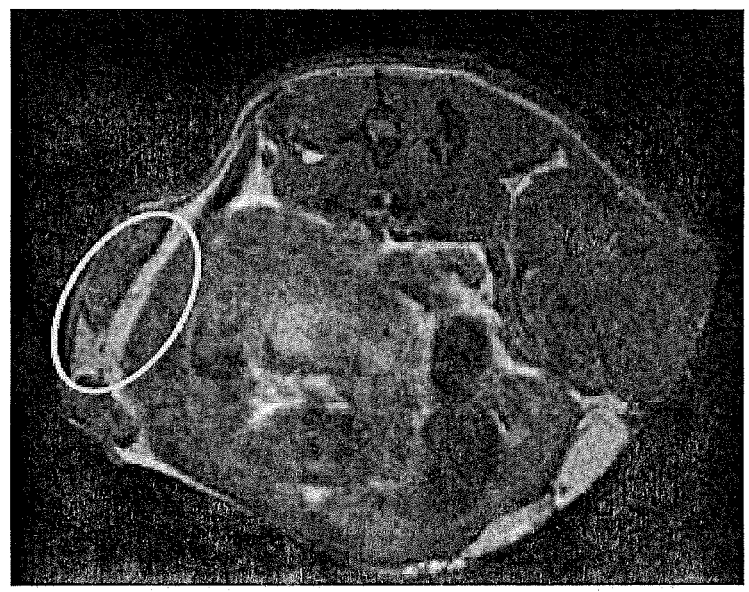
FIG. 8. In vivo magnetic resonance imaging (MRI) showed cartilage taking shape after 2-week implantation into nude mice.

Mechanical properties, cell viability, and cartilage production of the printed constructs were evaluated. The fabricated scaffolds demonstrated more stiffness and were able to withstand greater tensile stress than alginate hydrogels (FIG. 6). Over 81% of the cells within the construct maintained viability after printing. Histological analysis showed cartilage-specific ECM production (e.g. GAGs and type II and IV collagens) both in vitro (FIG. 7) and in vivo (FIG. 9), indicating the formation of cartilage tissues. In vivo magnetic resonance imaging (MRI) showed cartilage taking shape after 2-week implantation into nude mice (FIG. 8).

Materials and Methods

Polycaprolactone (PCL) (Mn 42,500) and Pluronic F-127 were obtained from Sigma-Aldrich (St. Louis, Colo.) and acetone from Fisher Chemicals (Fair Lawn, N.J.). Bovine fibrinogen and bovine thrombin were obtained from Sigma-Aldrich and rat tail. PCL (10% wt/wt) and Pluronic F-127 (5% w/w) were dissolved in acetone under gentle stir in a warm water bath (50° C.). The Pluronic F-127 in the polymer solution was used.

Chondrocytes were obtained from rabbits' ear cartilage as previously described (E. Sanz, L. Penas, J. L. Lequerica, *Plast Reconstr Surg* 2007, 119, 1707). Briefly, after sedation of the rabbit, the ear was shaved, cleaned with povidone-iodine, and draped. A pocket was resected under sterile conditions at the subperichondrial level and an approximately 2×2-cm piece of cartilage was removed. Biopsy specimens were washed in phosphate-buffered saline (Gibco-BRL, Grand Island, N.Y.) and finely minced under sterile conditions. Chondrocytes were released from the cartilage by enzymatic digestion with collagenase type B (Boehringer Mannheim GmbH, Germany). The minced cartilage was placed in tissue culture dishes containing 10 to 12 ml of Ham's F12 medium with glutamine/bicarbonate supplemented with 10% fetal bovine serum, 100 U/ml penicillin, 100 µg/ml streptomycin, 2.5 µg/ml amphotericin B (Gibco-BRL), and 1 mg/ml collagenase type B and incubated at 37° C. in an orbital shaker (Stuart Scientific, Surrey, United Kingdom). After 24 hours, the undigested pieces were discarded and the supernatant was seeded onto tissue culture dishes. Each dish was filled with 20 ml of fresh culture media and incubated in a humidified incubator at 37° C. with 5% CO2. Media was changed every 3 or 4 days. Culture medium was Dulbecco's modified eagle medium (DMEM) supplemented with 10% fetal bovine serum (FBS), 1% antibiotics, and 1% glutamine.

Rabbit chondrocytes were collected from the culture. After trypsinizing, cell pellets were collected and re-suspended in the mixture of fibrinogen (10 mg/ml)/collagen (1.5 mg/ml) in 1× phosphate buffer saline (PBS, Sigma-Aldrich) with the final concentration of 3-4×10$^6$ cells/ml.

Hybrid Printing System.

Figure 10:
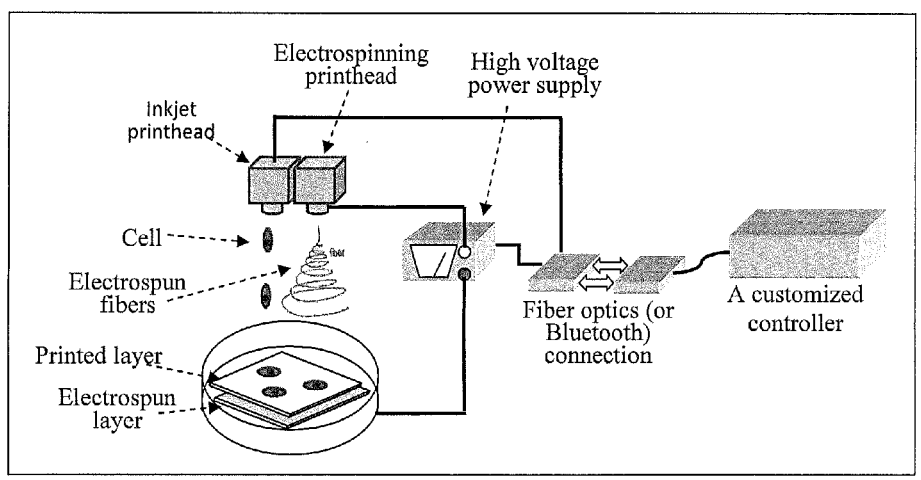
FIG. 10. Schematic diagram of printing apparatus according to some embodiments.

To build cartilage constructs, we have developed a hybrid printing system by incorporating the electrospinning apparatus into the inkjet printing platform. FIG. 10 shows the schematic drawing of this system.

The inkjet printing platform is composed of a customized XYZ plotter driven by the step motors and the print head equipped with a DC solenoid inkjet valve (Offshore Solutions Inc, Beaverton, Oreg.). A reservoir for loading cell print suspension is connected to the inkjet valve. By air pressure, the cell print suspension is supplied to the inkjet valve from reservoirs. The print head is mounted over a XYZ plotter platform to allow precise deposition of cells onto a scaffold generated by electrospinning. Positioning the XYZ plotter under the print head is controlled via a customized controller. The controller acquires the positioning information from software loaded on a computer. This software converts the image of the target to a special four byte protocol, which is used to activate specific inkjet valve and coordinate X-Y-Z position.

In this hybrid system, the electrospinning apparatus is used to generate polymeric fibers based scaffolds. An electrospinning head, in tandem with the inkjet head, is also mounted over the XYZ plotter. The high voltage power supply, used to provide a high voltage field for electrospinning, is modulated by the same customized controller.

To avoid the potential adverse effect caused by static discharge of high voltage on the logic circuitry of the customized controller, it is required to conductively isolate the controller from the high voltage power supply. For this purpose, we used fiber optics or Bluetooth to connect the control system to the high voltage power supply. The fiber optics use light transmission to receive or send the data between the control system and the high voltage power supply. In this way, the two systems can be effectively isolated.

Fabrication of Cartilage Constructs.

A layer of PCL was spun for 30 min at 3 mL/hr, and then the 3 mL of the print suspension containing cells and the fibrinogen/collagen mixture was printed through the inkjet valve onto the electro-spun PCL scaffold layer to form a cell/matrix layer. 1.5 mL thrombin (20 UI/ml dissolved in PBS) was subsequently printed on the cell/matrix layer to create a transient clot for structural integrity while spinning. Subsequently, PCL was spun for another 10 min at 3 mL/hr, and then inkjet printing of cell suspension was repeated. A final layer of PCL was spun for 30 min at 3 mL/hr.

Cell Viability.

The viability of chondrocytes within the fabricated cartilage constructs 1 days after culture was evaluated by a two-color fluorescence live/dead assay using a solution consisting of 2 µM calcein AM and 4 µM ethidium homodimer (EthD-1; Molecular Probes, Oreg.) in 10 ml Phosphate Buffered Saline (PBS). Printed samples with chondrocytes were rinsed to remove residual serum, and 2 ml of viability testing solution was added to each sample. The samples were incubated for 30 min at 37° C. followed by rinse with PBS. The samples were viewed using a fluorescent microscope and the viability of the cells was evaluated by counting the number of cells stained with calcein AM (green), and this number was compared to the total number of cells. 81.58+/−3.46% of the cells were alive after one week in vitro.

Mechanical Properties.

The constructs without cells fabricated by the hybrid printing method were mechanically loaded using a uniaxial load frame (Instron Corporation, Issaquah, Wash.). A short segment from the scaffold was clamped at its cut ends for the axial test. The crosshead speed was set at 0.2 mm/s, and the test was stopped when the force decreased by 10% after the onset of failure. Young's modulus (modulus of elasticity) was calculated from the slope of the initial linear segment of the stress-strain curve at maximum stress. Ultimate tensile stress (UTS, MPa) at break was calculated as the maximal load recorded during each test.

As shown in Table 1, mechanical testing demonstrated that the fabricated hybrid scaffold has more stiffness and is able to withstand greater stress than alginate and PCL.

TABLE 1

Mechanical Testing of Fabricated Scaffolds

|  | Alginate | PCT | Scaffold |
|---|---|---|---|
| Young's Modulus (MPa) | 0.409 ± 0.060 | 0.709 ± 0.215 | 1.764 ± 0.704 |
| Ultimate Tensile Strength (MPa) | 0.241 ± 0.082 | 0.913 ± 0.165 | 1.113 ± 0.124 |
| Elasticity | 0.421 ± 0.074 | 1.095 ± 0.089 | 0.552 ± 0.209 |

Microscopy.

The microstructures of the cartilage constructs was evaluated by using Scanning electron microscopy. Cross-sectional electron-micrographs were obtained at 25.0 kV, 50 Pa, 500× magnification using a Hitachi S-2600 Scanning Electron Microscope (Hitachi High Technologies America, Pleasanton, Calif.). Microscopy revealed that the layered structure was maintained (FIG. 4). The microstructure of the PCL was also examined an high magnification (4000×), and was seen to be fibrous with beads. SEM analysis also demonstrated attachment of chondrocytes to the matrix and extracellular matrix deposition (FIG. 5).

In Vivo Evaluation.

All animal procedures were performed according to the protocols set by the Wake Forest University Health Sciences Animal Care and Use Committee. The fabricated cartilage constructs were implanted subcutaneously into the back of outbred athymic nude (nu/nu) mice (Charles River Laboratories). Four printed constructs were implanted per mouse. The samples were retrieved after 8 weeks of implantation and evaluated.

MRI characterization of implanted tissues on animals was performed at 2 and 10 weeks after implantation. Experiments were performed using a 7T small animal MRI scanner (Bruker Biospin Inc., Billerica, Mass.), with an actively-shielded gradient set capable of a maximum gradient of 400 mT/m. A custom-made Litz volume coil with 25 mm ID (Doty Scientific Inc., Columbia, S.C.) was used for both signal transmission and reception. The animals were anesthetized with 3% isoflurane and oxygen at a flow rate of 3 L/min initially, and then maintained with a mixture of 1.5% isoflurane and oxygen at a flow rate of 1 L/min through a nose cone while in the scanner. The respiration and ECG of the animals were monitored (SA Instruments Inc, Stoney Brook, N.Y.) throughout the scan. Cartilage implants were identified on T2-weighted multi-slice fast spin-echo Rapid Acquisition with Relaxation Enhancement (RARE) images with the following parameters: TR/TE=2500/42 ms, number of echoes, 4, 2 NEX, image matrix 256×256, slice thickness 0.6 mm, field of view (FOV) 4 cm.

Histology.

The printed samples were both cultured for four weeks in vitro and implanted for 8 weeks in vivo were histologically evaluated. The printed implants were surgically removed from the implantation sites 8 weeks after implantation. All samples were fixed overnight with 10% formalin. After being embedded in paraffin, these samples were cut into 3-5 μm thick sections. Cartilage production was determined by a Masson's Trichrome (MT) stain for collagen and a Safranin O (Saf O) stain for glycosaminoglycans. In order to identify different collagen types produced within the constructs, the printed samples were immunostained with anti-Type II collagen antibodies and anti-Type IV collagen antibodies (Dako, Denmark).

Histological analysis of the in vitro cultured samples showed that the chondrocytes maintained their phenotype and were able to produce cartilage after 4 weeks. Analysis of sections taken after 2 weeks in vitro showed the initiation of cartilage tissue formation (not shown). The cartilage construct at 4 weeks demonstrated a significant population of chondrocytes as well as deposition of cartilage tissue matrix (FIG. 7). Masson's Trichrome staining showed bands of collagen accumulated around the cells. Safranin O staining demonstrated the production of glycosaminoglycans. In cartilage, the principle GAGS are chondroitin sulfate and keratan sulfate, which are markers of ECM deposition. Immunohistochemical analysis of the deposited collagen revealed both type II and IV collage, which are major components of cartilage (FIG. 7). Control samples demonstrated little, if any, collagen and GAGs.

Figure 9:
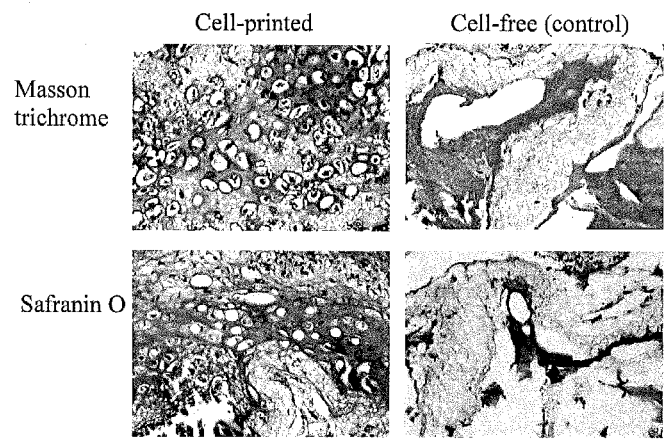
FIG. 9. Hybrid constructs produced cartilage-specific matrix in vivo. Masson trichrome and safranin O staining of printed constructs 8 wks post-implantation.

The printed samples developed into cartilage-like constructs in vivo. Histological analysis showed that printed chondrocytes maintained their phenotypic characteristics and formed cartilage tissue 8 weeks post-implantation in vivo. Masson's Trichrome staining showed collagen production by the cells in vivo (FIG. 9). Similarly, safranin O staining confirmed the production of glycosaminoglycans. Control samples failed to produce any collagen or GAGs (data not shown).

Compared to the in vitro conditions, larger amounts of collagen and GAG were seen in the implant. Moreover, in the implant, the typical cartilage lacunae structure was found in the samples, and many chondrocytes situated in these lacuna. Taken together, these data suggest that more mature cartilage tissues were developed in the in vivo than in the in vitro conditions.

Example 2

High-Throughput Production of Single Cell Microparticles Using Inkjet Printing

An insulin-producing beta cell line (TC6) was obtained from American Type Culture Collection (ATCC, Manassas, Va.). The cells were maintained in Dulbecco's Modified Eagles Medium (ATCC) supplemented with heat-inactivated 10% fetal bovine serum (Invitrogen, Carlsbad, Calif.), 100 IU of penicillin (Invitrogen) and 100 μg/ml of streptomycin (Invitrogen) and incubated at 37° C. in a humidified 5% CO2 atmosphere.

Sodium alginate (MVG; Pronova Biomedical, Oslo, Norway) with an overall gluronic acid (G-block) content of 70% (as reported by the manufacturer) was mixed with PBS at different concentrations (0.5%, 1%, and 2% solution (w/v)) and autoclaved. Beta-TC6 cells were trypsinized, cell pellets collected and re-suspended in sodium alginate solutions at different final cell concentrations ($2 \times 10^6$, $6 \times 10^6$, and $12 \times 10^6$ cells/ml).

HP DeskJet 550C printers were modified using previously described methods (Xu et al., 2005, "Inkjet printing of viable mammalian cells," Biomaterials, 26(1), pp. 93-99). Commercial inkjet cartridges (HP51626A) were emptied and rinsed thoroughly with distilled water and 70% ethanol. The entire printer assembly, including the cartridges, was kept in a laminar flow biosafety cabinet under ultraviolet light overnight prior to use. A pattern that consisted of rows of rectangles was designed using the Microsoft Word software (Microsoft, Redmond, Wash.). The alginate/cell print suspensions were loaded into the cartridges and printed drop-by-drop into 35-mm petri dishes, which contained $CaCl_2$ solutions at different ionic strengths (0.05M, 0.1M, 0.5M, and 1M). A magnetic stir system was mounted under the inkjet printer and used to prevent aggregation of micro-particles during the printing process. Subsequently, the $CaCl_2$ solutions were removed from the Petri dishes and culture medium was carefully introduced. The samples were maintained at standard culture conditions.

Using this modified HP DeskJet 550C printer, alginate microparticles containing one to several insulin producing cells (beta-TC6) were fabricated by printing a composition with the cells and sodium alginate suspension into a $CaCl_2$ solution, generating microparticles of 30-60 μm in diameter at a rate as high as 55,000 particles per second. Cell survival assays showed that more than 89% of printed cells survived the fabrication process.

The effects of varying print conditions on cell distribution and morphology of the printed microparticles were evaluated by changing sodium alginate concentrations, $CaCl_2$ concentrations, and/or cell concentrations for printing. The efficiency of the fabrication method was evaluated by counting the total number of particles with respect to time.

The viability of the beta-TC6 cells contained in the printed alginate microparticles was evaluated by a two-color fluorescence live/dead assay using a solution consisting of 2 μM calcein AM and 4 μM ethidium homodimer (EthD-1; Molecular Probes, Oreg.) in 10 ml phosphate buffered saline (PBS). Printed samples with beta-TC6 cells were rinsed to remove residual serum, and 2 ml of viability testing solution was added to each sample. The samples were incubated for 30 min at 37° C. followed by rinse with PBS. The samples were viewed using a fluorescent microscope and the viability of the cells was evaluated by counting the number of cells stained with calcein AM (green), and this number was compared to the total number of cells. The viability results of the printed samples were compared with the controls, in which beta-TC6 cells were manually plated onto a standard tissue culture plate (BD Biosciences, San Jose, Calif.).

The insulin secreted from the printed cell particles was analyzed with an ultrasensitive mouse insulin enzyme-linked immunosorbent assay (ELISA) kit (Mercodia, N.C.). The media was changed every two days and collected 4 and 6 days after culture for analysis. As per the manufacturer's protocol, insulin levels were detected upon comparison of the unknown samples to the provided standards. The ELISA procedure consisted of a 2 hour incubation of unknown and standard samples with an enzyme conjugated insulin-specific antibody, followed by 6 washes and a final incubation with the soluble substrate 3-3', 5-5' tetramethylbenzidine (TMB) before reading at 450 nm.

All results were presented as mean±standard deviation. The grouped data were statistically compared with Analysis of Variance (ANOVA) and a two-sample Student's t-test.

The printed beta-TC6 cells demonstrated continuous insulin secretion over a 6-day period, which suggests that the printed cells are able to maintain normal cellular function within the microparticles.

The printing conditions, such as cell number, alginate concentration, and ionic strengths of $CaCl_2$, influenced cellular distribution and geometry of the printed particles. The droplets ejected from an inkjet printer according to this Example range from 8 to 95 pL (Xu et al., 2004, "Construction of high-density bacterial colony arrays and patterns by the inkjet method," Biotechnol Bioeng, 85(1), pp. 29-33), which permit the generation of micro-scale particles that contain single cells. Furthermore, the printing process according to this Example involves a high firing frequency (5-20 kHz) that can produce over 250,000 droplets per second (Xu et al., 2006, "Viability and electrophysiology of neural cell structures generated by the inkjet printing method," Biomaterials, 27(19), pp. 3580-3588), which is suitable for high throughput production of micro-particles.

Figure 11:
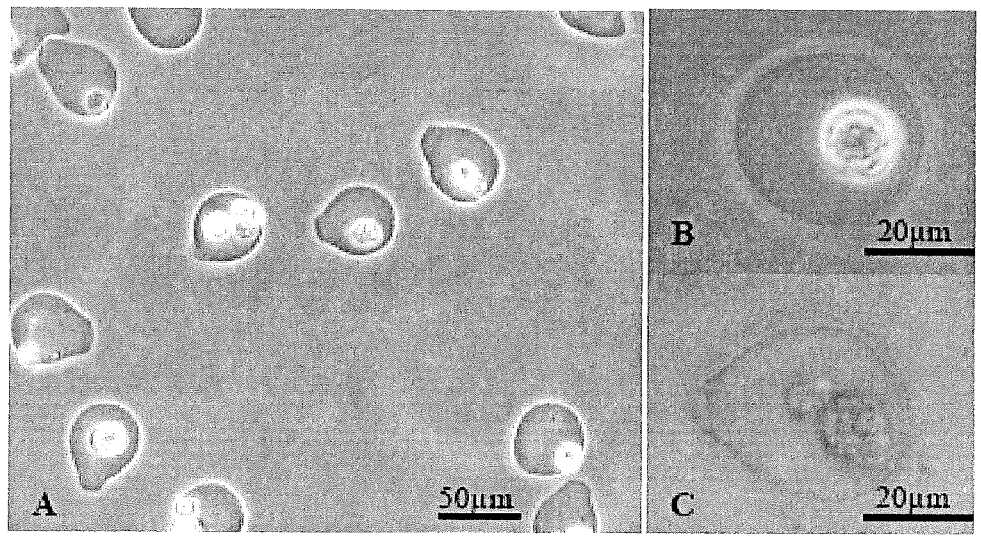
FIG. 11. Phase contrast images of printed beta-TC6 cell microparticles. (A): Many individual particles were dispersed in medium 1 day after culture. Most particles contained single or just a few cells, and very few particles were without cells. (B): High magnification of a microparticle containing a single cell 1 day after culture. (C): Individual microparticle contained beta-TC6 cells 1 month after culture. The microparticle maintained its original structure and the cells were still entrapped inside the particle. Magnifications are as follows: 100×(A) and 400×(B and C).

The printing process readily produced microparticles that contained single or a few cells, indicating that printing techniques can be used for direct production of cell-containing microparticles. FIG. 11 shows the morphology of the printed cell microparticles. Most particles contained single to just a few cells, and only a small number of particles was found empty (FIG. 11).

The stability of the printed alginate particles was evaluated by culturing the printed microparticle samples over a period of 1 month. The microparticles maintained their structural integrity, and the cells remained viable within each particle. The production rate was measured by counting the total number of printed microparticles with respect to time. The calculations showed that the thermal inkjet printer was able to generate cell-containing microparticles at a rate of approximately 55,000 microparticles per second.

Figure 12:
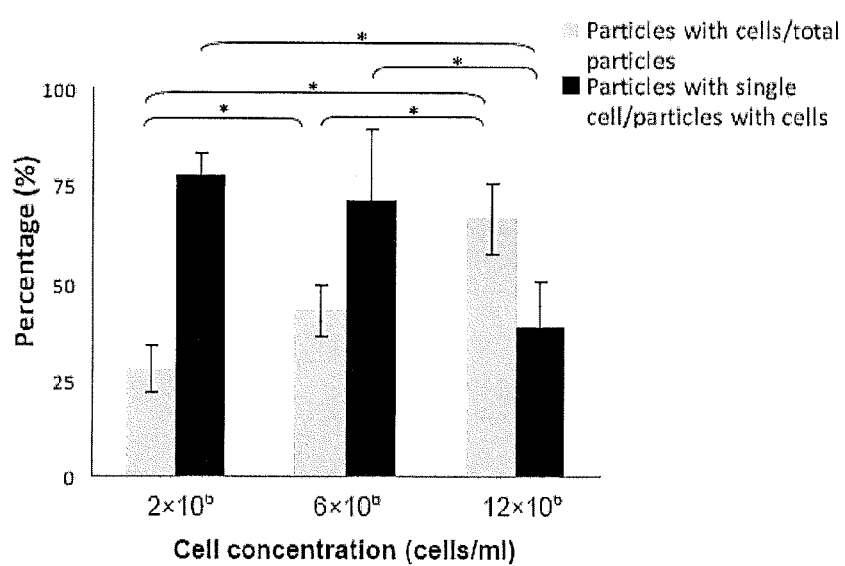
FIG. 12. The number of entrapped cells with respect to varying cell concentrations. As the cell concentration in the print solution increased, the number of printed particles containing cells increased (shown in gray bars). However, the number of microparticles containing only a single cell decreased significantly with increase in cell concentration (shown in black bars). (* $P<0.01$, n=10).

To determine the effects of cell concentration on the number of cells encapsulated within the printed microparticles, print suspensions with different beta-TC6 cell concentrations ($2\times10^6$, $6\times10^6$, and $12\times10^6$ cells/ml) were tested. The number of cells within the printed microparticle increased as the cell concentration in the print solution increased. However, the number of microparticles containing only a single cell decreased significantly with increase in cell concentration (FIG. 12) ($p<0.01$, $n=10$). The concentration of $6\times10^6$ cells/ml resulted in one or more cells being present in about 50% of all particles. Of those cell-containing particles, about 70% contained a single cell. These findings indicate that an appropriate concentration of cells in the printing solution would permit a high yield of microparticles containing single cells.

Figure 13:
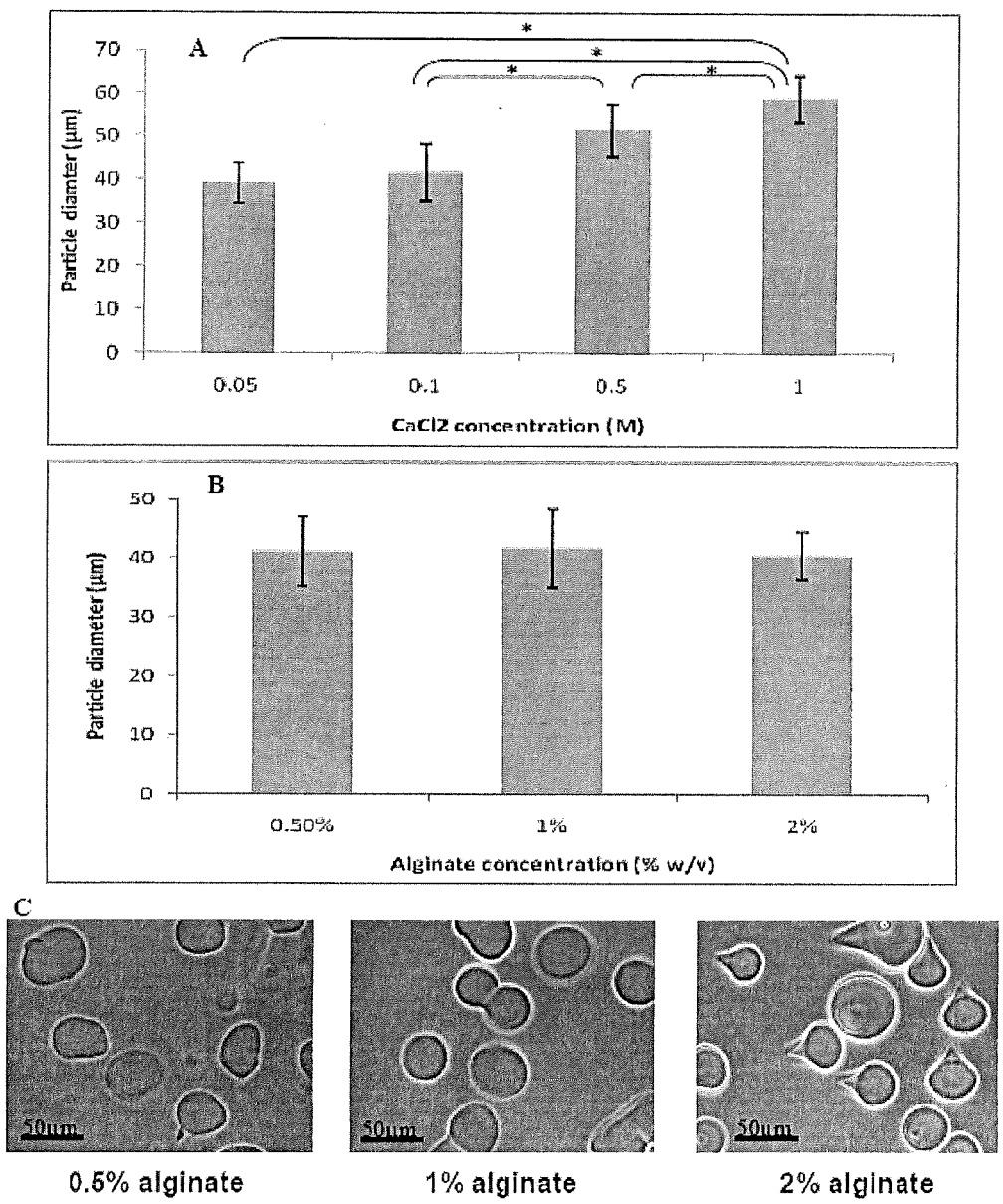
FIG. 13. The effects of printing parameters on particle geometry. As $CaCl_2$ ionic strength increased, the diameter of the printed particles increased (A). Increases in the alginate concentration did not change the particle diameter significantly (B). However, changes in the alginate concentration resulted in dramatic variation in the particle geometries (C). Most particles printed from 1% alginate showed round structures, while most particles generated from 0.5% alginate produced irregular shapes (C). Particles from 2% alginate showed long tailed structures (C). (* $P<0.01$, n=10). Magnification: 100×.

The effects of printing parameters on microparticle geometry were also investigated using different ionic strengths of $CaCl_2$ solutions. Although the printed particles had similar shapes in each $CaCl_2$ solution, the diameter of the particles was dependent on the $CaCl_2$ ionic strength. As shown in FIG. 13A, the printed particles had relatively larger diameters when higher $CaCl_2$ ionic strength was used ($p<0.01$, $n=10$), In contrast, an increase in the alginate concentration did not change the particle diameter significantly (FIG. 13B) ($p>0.01$, $n=10$). However, changes in the alginate concentration caused a marked variation in particle geometry (FIG. 13C). Most particles printed from 1% alginate were found as round structures, while most particles generated from 0.5% alginate were shaped irregularly. Microparticles from 2% alginate demonstrated long tailed shapes, suggesting that the viscosity of the alginate solution used may play a role in the final outcome of particle geometry.

Figure 14:
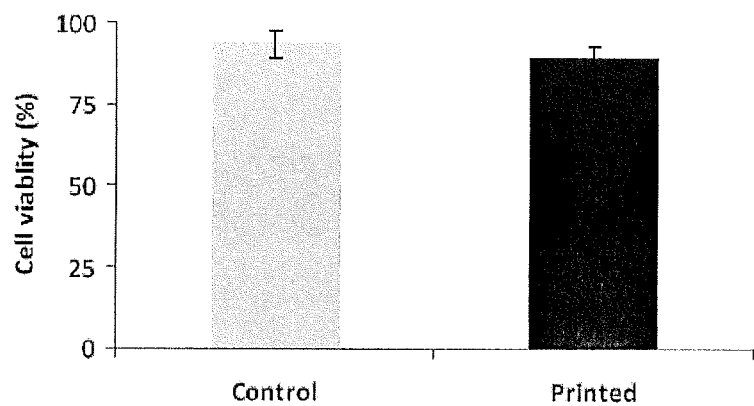
FIG. 14. Viability of the cell-loaded micro-particles 1 day after printing. The printed particles showed similar mean viability as the controls (p>0.05, n=10), which were prepared by manually seeding beta-TC6 cells onto standard tissue culture plates.

Survival rate of the printed beta-TC6 cells within the particles was analyzed by a commercial cell survival assay and compared with the controls ($n=10$), which were prepared by manually placing the cells onto standard tissue culture plates. The cell/dead assay showed that more than 89% of printed cells remained viable within the microparticles 1 day after printing (FIG. 14). The printed control particles showed similar viability (93.1±4.6%) ($P>0.05$, $n=10$).

Figure 15:
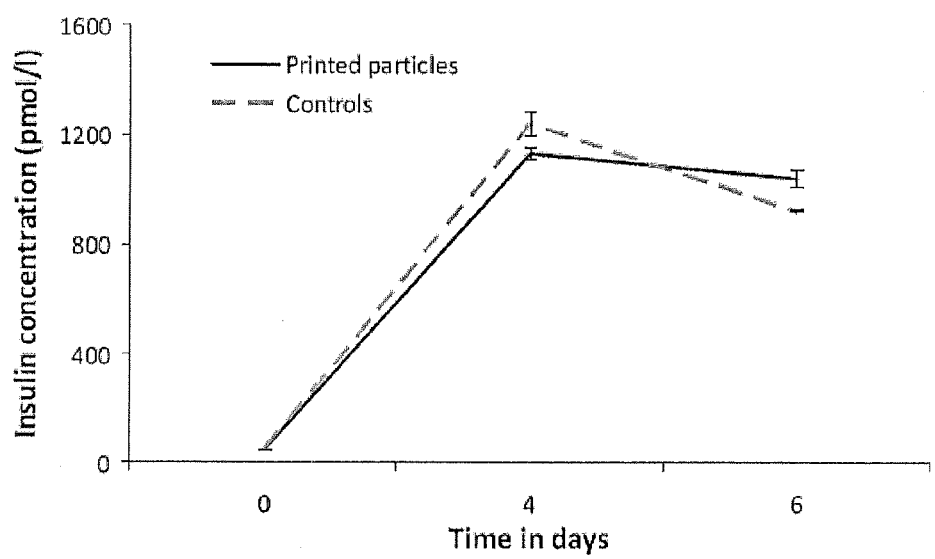
FIG. 15. The insulin secretion profiles for the cultures of beta-TC6 cell-containing microparticles and the controls over a 6-day period. The printed beta-TC6 cells displayed a continuous insulin secretion during this time. The secreted insulin concentrations from the printed particles were comparable to that of the control group, which were prepared by manually seeding beta-TC6 cells onto standard tissue culture plates.

To determine whether normal cell function can be retained throughout the printing process, microparticles containing cells were analyzed for insulin production using an ultrasensitive ELISA method. The insulin secretion profiles for cultures of beta-TC6 cell-containing microparticles displayed a continuous insulin secretion pattern during the entire 6-day period of the study. The secreted insulin concentrations from the printed particles were similar to non-printed controls, which were prepared by manually placing the cells onto standard tissue culture plates. This indicates that normal cellular function can be preserved by the inkjet printing technique (FIG. 15).

Inkjet printing is considered to be one of the most promising new methods for the selective and precise deposition of functional materials to target locations (Park et al., 2006, "Control of colloidal particle deposit patterns within picoliter droplets ejected by ink-jet printing," Langmuir, 22(8), pp. 3506-3513). The print heads of a thermal inkjet printer are typically equipped with 30-200 μm capillary channels (Ringeisen et al., 2006, "Jet-based methods to print living cells," Biotechnol J, 1(9), pp. 930-948) to allow for the delivery of individual droplets with small volumes ranging from 8 to 95 pL per droplet (Xu et al., 2004, "Construction of high-density bacterial colony arrays and patterns by the ink-jet method," Biotechnol Bioeng, 85(1), pp. 29-33). This unique feature permits the inkjet printer to serve as a micro-fabrication tool for the generation of micro-scale particles.

We hypothesized that cells would become entrapped within the droplets during printing and produce single-cell containing microparticles if both droplets and cells were printed simultaneously. In this study we demonstrate that insulin producing beta-TC6 cells can be combined with alginate solutions and printed into $CaCl_2$ solutions. We show that printed alginate microparticles are able to entrap a single to several cells that can be maintained stably for up to one month post-printing.

The ability to control the size of the printed particles is critical for application in vivo. The diameter of individual mammalian cells in an unattached status generally ranges from 10-30 μm. Therefore, the size of the particles generated by the printing method in this study is comparable to these cells, considering the actual size ranges that were fabricated in this study. However, the size of the particles can be controlled by modifying the printing parameters such as varying the ionic strengths of $CaCl_2$ solution. These diameter differences may be due to the surface gelling mechanism, in which higher $CaCl_2$ ionic strengths result in immediate gelling at the surface with minimal penetration of Ca++ ions into the alginate droplets (Boland et al., 2006, "Application of inkjet printing to tissue engineering," Biotechnol J, 1(9), pp. 910-917). The reduced diameter of the microparticles, which approximates that of a single cell, may extend the viability and function of the entrapped cells within the microparticles.

The foregoing is illustrative of the present invention, and is not to be construed as limiting thereof. The invention is defined by the following claims, with equivalents of the claims to be included therein.

That which is claimed is:

1. A method of forming microparticles comprising one or more cells encapsulated by a substrate, said method comprising printing a composition comprising said cells and said substrate into a solution that promotes gelling of the substrate, wherein said substrate comprises alginate, and wherein said solution that promotes gelling of the substrate comprises divalent cations, to thereby form said microparticles, wherein said microparticles comprise a membrane of said substrate encapsulating 10 cells or less in at least 50% of the printed cells.

2. The method of claim 1, wherein said divalent cations comprise $Mg^{2+}$, $Ca^{2+}$, $Sr^{2+}$ and/or $Ba^{2+}$.

3. The method of claim 1, wherein said microparticles have an average diameter of from 5 to 50 micrometers.

4. The method of claim 1, wherein greater than 50% of said microparticles formed contain a single cell encapsulated by said substrate.

5. The method of claim 1, wherein said cells are selected from the group consisting of pancreas cells, kidney cells, liver cells and nerve cells.

6. The method of claim 1, wherein said cells are pancreatic islet cells.

7. The method of claim 6, wherein said pancreatic islet cells secrete insulin.

8. The method of claim 1, further comprising the steps of:
providing an inkjet printing device, said device comprising at least one inkjet printer cartridge; and
loading a composition comprising said cells and said substrate into said printer cartridge, prior to said printing step.

9. The method of claim 8, wherein said cells are included at a concentration of between $10^5$ and $10^7$ cells per milliliter of said composition.

10. The method of claim 8, wherein said substrate is alginate and said composition comprises between 0.5 and 2% w/v of said substrate.

11. The method of claim 1, wherein more than 80% of said cells by number are viable 24 hours after printing.

12. A method of forming an array of microparticles comprising one or more cells encapsulated by a substrate comprising the steps of:
providing an inkjet printing device, said device comprising at least one inkjet printer cartridge;
loading a composition comprising said cells and said substrate into said printer cartridge; wherein said substrate comprises alginate; and
printing said composition in an organized pattern into a solution that promotes gelling of the substrate, wherein said solution comprises divalent cations, to thereby form said array of microparticles,
wherein said microparticles comprise a membrane of said substrate encapsulating 10 cells or less in at least 50% of the printed cells.

13. The method of claim 12, wherein said microparticles have an average diameter of from 5 to 50 micrometers.

14. The method of claim 12, wherein greater than 50% of said microparticles contain a single cell encapsulated by said substrate.

15. The method of claim 12, wherein said cells are selected from the group consisting of pancreas cells, kidney cells, liver cells and nerve cells.

16. The method of claim 12, wherein said cells are pancreatic islet cells.

17. The method of claim 12, wherein said cells secrete insulin.

18. The method of claim 12, wherein said divalent cations comprise $Mg^{2+}$, $Ca^{2+}$, $Sr^{2+}$ and/or $Ba^{2+}$.

19. The method of claim 12, wherein said cells of said loading step are included at a concentration of between $10^5$ and $10^7$ cells per milliliter of said composition.

20. The method of claim 12, wherein said substrate is alginate and said composition of said loading step comprises between 0.5 and 2% w/v alginate.

21. The method of claim 12, wherein more than 80% of said cells by number are viable 24 hours after printing.

* * * * *